(12) United States Patent
Petersen et al.

(10) Patent No.: US 7,371,409 B2
(45) Date of Patent: *May 13, 2008

(54) BONE GRAFT SUBSTITUTE COMPOSITION

(75) Inventors: Donald W. Petersen, Bessemer, AL (US); Barbara E. Blum, Memphis, TN (US)

(73) Assignee: Wright Medical Technology, Inc., Arlington, TN (US)

(*) Notice: Subject to any disclaimer, the term of this patent is extended or adjusted under 35 U.S.C. 154(b) by 1150 days.

This patent is subject to a terminal disclaimer.

(21) Appl. No.: 09/947,833

(22) Filed: Sep. 6, 2001

(65) Prior Publication Data

US 2003/0050710 A1 Mar. 13, 2003

(51) Int. Cl.
A61D 35/32 (2006.01)

(52) U.S. Cl. ........... 424/549; 424/682; 424/696; 623/16.11; 623/23.51; 623/23.61; 623/23.62; 623/23.63

(58) Field of Classification Search ........... 424/549, 424/682, 696
See application file for complete search history.

(56) References Cited

U.S. PATENT DOCUMENTS

| | | | |
|---|---|---|---|
| 4,430,760 A | 2/1984 | Smestad | |
| 4,568,536 A | 2/1986 | Kronenthal et al. | |
| 4,595,713 A | 6/1986 | St. John | |
| 4,596,574 A | 6/1986 | Urist | |
| 4,612,009 A | 9/1986 | Drobnik et al. | |
| 4,619,655 A | 10/1986 | Hanker et al. | |
| 4,650,665 A | 3/1987 | Kronenthal et al. | |
| 4,681,763 A | 7/1987 | Nathanson et al. | |
| 4,820,306 A | 4/1989 | Gorman et al. | |
| 4,880,660 A | 11/1989 | Aasen et al. | |
| 4,882,149 A | 11/1989 | Spector | |
| 4,892,734 A | 1/1990 | Leonard | |
| 4,975,526 A | 12/1990 | Kuberasampath et al. | |
| 4,994,030 A | 2/1991 | Glowczewskie, Jr. et al. | |
| 5,061,286 A | 10/1991 | Lyle | |
| 5,073,373 A | 12/1991 | O'Leary et al. | |
| 5,147,403 A | 9/1992 | Gitelis | |
| 5,162,114 A | 11/1992 | Kuberasampath et al. | |
| 5,219,897 A | 6/1993 | Murray | |
| 5,236,456 A | 8/1993 | O'Leary et al. | |
| 5,236,971 A | 8/1993 | Murray | |
| 5,264,214 A | 11/1993 | Rhee et al. | |
| 5,284,655 A | 2/1994 | Bogdansky et al. | |
| 5,290,558 A | 3/1994 | O'Leary et al. | |
| 5,298,254 A | 3/1994 | Prewett et al. | |
| 5,306,304 A | 4/1994 | Gendler | |
| 5,314,476 A | 5/1994 | Prewett et al. | |
| 5,320,844 A | 6/1994 | Liu | |
| 5,336,699 A | 8/1994 | Cooke et al. | |
| 5,356,629 A | 10/1994 | Sander et al. | |
| 5,366,507 A | 11/1994 | Sottosanti | |
| 5,385,887 A * | 1/1995 | Yim et al. ............ 514/12 | |
| 5,405,390 A | 4/1995 | O'Leary et al. | |
| 5,417,975 A | 5/1995 | Lussi et al. | |
| 5,425,769 A | 6/1995 | Snyders, Jr. | |
| 5,439,684 A | 8/1995 | Prewett et al. | |
| 5,462,722 A | 10/1995 | Liu et al. | |
| 5,482,551 A | 1/1996 | Morris et al. | |
| 5,484,601 A | 1/1996 | O'Leary et al. | |
| 5,507,813 A | 4/1996 | Dowd et al. | |
| 5,510,396 A | 4/1996 | Prewett et al. | |
| 5,512,610 A | 4/1996 | Lin | |
| 5,531,791 A | 7/1996 | Wolfinbarger, Jr. | |
| 5,569,308 A | 10/1996 | Sottosanti | |
| 5,573,771 A | 11/1996 | Geistich et al. | |
| 5,578,662 A | 11/1996 | Bennett et al. | |
| 5,614,206 A | 3/1997 | Randolph et al. | |
| 5,618,549 A | 4/1997 | Patat et al. | |
| 5,676,146 A | 10/1997 | Scarborough | |
| 5,681,873 A | 10/1997 | Norton et al. | |
| 5,697,981 A | 12/1997 | Ison et al. | |
| 5,700,289 A | 12/1997 | Breitbart et al. | |
| 5,707,962 A | 1/1998 | Chen et al. | |
| 5,727,945 A | 3/1998 | Dannenbaum | |
| 5,756,127 A | 5/1998 | Grisoni et al. | |
| 5,763,416 A | 6/1998 | Bonadio et al. | |
| 5,766,618 A | 6/1998 | Laurencin et al. | |
| 5,769,897 A | 6/1998 | Harle | |
| 5,788,976 A | 8/1998 | Bradford | |
| 5,807,567 A | 9/1998 | Randolph et al. | |
| 5,824,087 A | 10/1998 | Aspden et al. | |
| 5,830,493 A | 11/1998 | Yokota et al. | |
| 5,861,445 A | 1/1999 | Xu et al. | |
| 5,899,939 A | 5/1999 | Boyce et al. | |
| 5,910,315 A | 6/1999 | Stevenson et al. | |
| 5,948,426 A | 9/1999 | Jefferies | |
| 5,948,428 A | 9/1999 | Lee et al. | |
| 5,964,805 A | 10/1999 | Stone | |
| 5,972,368 A | 10/1999 | McKay | |
| 5,981,828 A | 11/1999 | Nelson et al. | |
| 6,030,635 A | 2/2000 | Gertzman et al. | |
| 6,030,636 A | 2/2000 | Randolph et al. | |

(Continued)

FOREIGN PATENT DOCUMENTS

DE 196 20 117 C1 7/1997

(Continued)

OTHER PUBLICATIONS

Wilkins et al, Annales Chirurgiae et Gynaecologiae, 1999, vol. 88, pp. 180-185.*

(Continued)

Primary Examiner—Leon B. Lankford, Jr.
Assistant Examiner—Allison M. Ford
(74) Attorney, Agent, or Firm—Alston & Bird LLP

(57) ABSTRACT

A bone graft substitute composition can include essentially of calcium sulfate, a mixing solution, and a plasticizing substance. A bone graft substitute composition can include calcium sulfate, demineralized bone matrix, cancellous bone, a plasticizing substance, and a mixing solution.

26 Claims, 1 Drawing Sheet

U.S. PATENT DOCUMENTS

| | | | |
|---|---|---|---|
| 6,037,519 | A | 3/2000 | McKay |
| 6,051,247 | A | 4/2000 | Hench et al. |
| 6,056,970 | A | 5/2000 | Greenawalt et al. |
| 6,071,530 | A | 6/2000 | Polson et al. |
| 6,083,522 | A | 7/2000 | Chu et al. |
| 6,118,043 | A | 9/2000 | Nies et al. |
| 6,224,635 | B1 | 5/2001 | Ricci et al. |
| 2002/0016636 | A1 | 2/2002 | Ricci et al. |

FOREIGN PATENT DOCUMENTS

| | | | |
|---|---|---|---|
| GB | 999487 | * | 7/1965 |
| GB | 2 093 348 A | | 9/1982 |
| WO | WO 89/04646 A1 | | 6/1989 |
| WO | WO 96/39203 | | 12/1996 |
| WO | 9840113 | * | 9/1998 |
| WO | WO 98/40113 | | 9/1998 |
| WO | WO 99/15150 A1 | | 4/1999 |
| WO | WO 02/05750 A2 | | 1/2002 |

OTHER PUBLICATIONS

Hanker et al., "Setting of Composite Hydroxylaptie/Plaster Implants with Blood for Bone Reconstruction," Proceedings of the 44th Annual Meeting of the Electron Microscopy Society of America, 1986.

Grimandi et al., "In vitro evaluation of a new injectable calcium phosphate material", *J. Biomed. Mater Res.*, 1998, pp. 660-666, vol. 39, John Wiley & Sons, Inc.

Advances in Biomaterials for Bone Regeneration, Orthopedics, vol. 26, No. 5/Supplement, May 2003.

Randal R. Betz, M.D., "Limitations of Autograft and Allograft: New Synthetic Solutions", Orthopedics, vol. 25, No. 5, Supplement May 2002.

"Bone Graft Substitutes Safe, Effective", AMA Science News Media Briefings, Dec. 6, 2001.

Turner et al., "Radiographic and Histologic Assessment of Calcium Sulfate in Experimental Animal Models and Clinical use as a Resorbable Bone-Graft Substitute, A Bone-Graft Expander, and a Method for Local Antibiotic Delivery", The Journal of Bone and Joint Surgery, Incorporated, vol. 83-A, Supp. 2, Part 1, 2001.

Greenwald et al., "Bone-Graft Substitutes: Facts, Fictions, and Applications", The Journal of Bone & Joint Surgery, JBJS Org., vol. 83-A, Supplement 2, Part 2, 2001.

Evelyn B. Kelly, Ph.D., "New Frontiers in Bone Grafting", Orthopaedic Technology Review, vol. 2, No. 9, Oct. 2000.

Adkisson et al., "Rapid Quantitative Bioassay of Osteoinduction", Journal of Orthopaedic Research, 18:503-511, 2000.

Biomaterials Tutorial, www.btec.cmu.edu/tutorial/biomaterials/biomaterials.htm, undated.

* cited by examiner

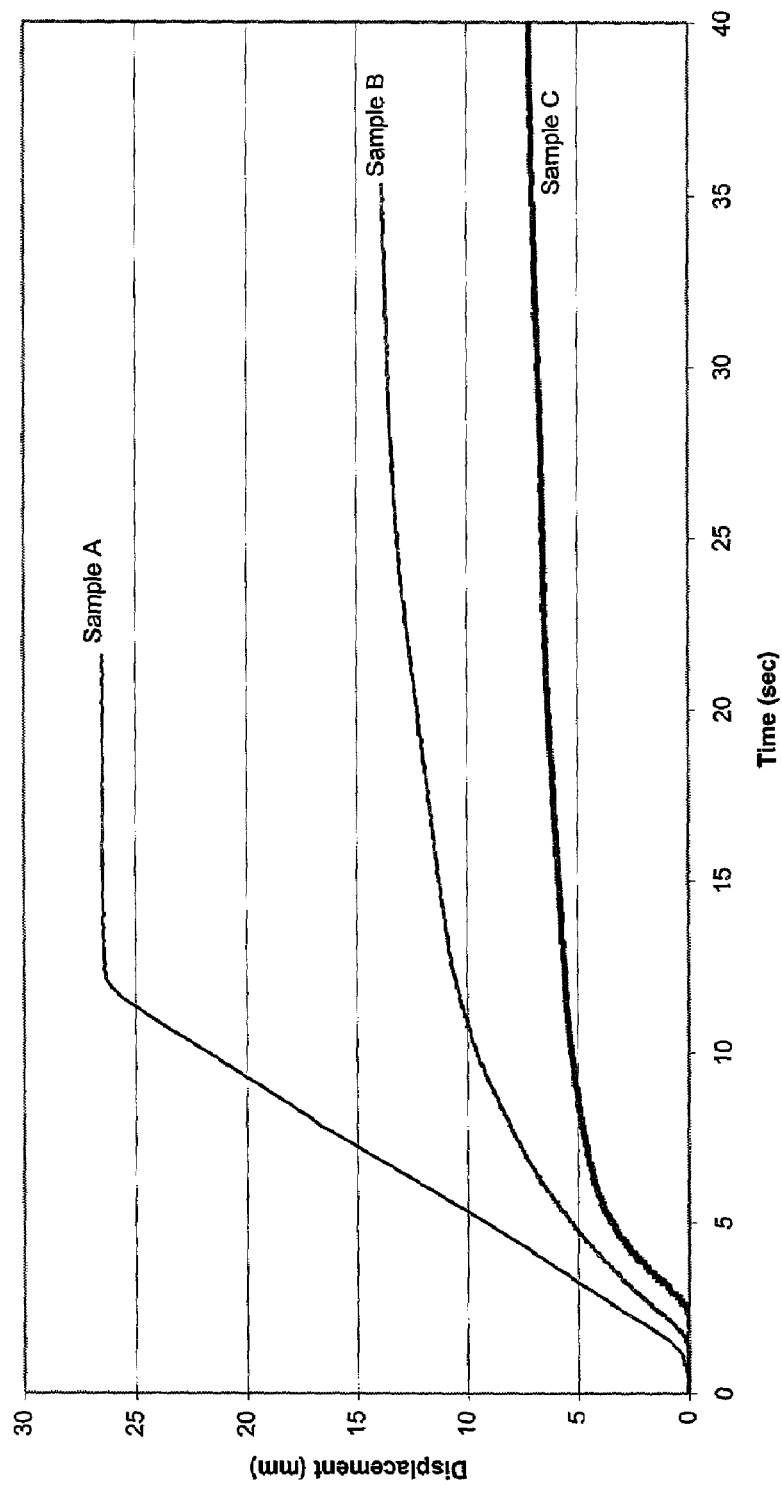
FIGURE

BONE GRAFT SUBSTITUTE COMPOSITION

FIELD OF THE INVENTION

The invention relates to bone graft substitute compositions.

BACKGROUND

Calcium sulfate has been clinically used for many years as a bone void filler with successful results. A preliminary patentability search produced the following patents which appear to be relevant to the present invention:

Hanker et al., U.S. Pat. No. 4,619,655, issued Oct. 28, 1986, discloses an animal implant comprising a scaffold material composed of plaster of Paris and a non-bioresorbable calcium material (such as calcium phosphate ceramic particles) bound with the plaster of Paris; a method of inserting such a composition in fluid or semisolid form into the appropriate body location of an animal (e.g., about a fracture locus); and a method of inserting a preform of such composition into the appropriate location of an animal (e.g., at the locus of a fracture).

Gitelis, U.S. Pat. No. 5,147,403, issued Sep. 15, 1992, discloses a method or technique for implanting a prosthesis comprising the steps of first preparing the surface of a bone to receive the prosthesis, then applying a calcium sulfate suspension in free flowing form to the prepared bone surface, and then seating the prosthesis to the coated bone surface.

Randolph, U.S. Pat. No. 5,614,206, issued Mar. 25, 1997, and U.S. Pat. No. 5,807,567, issued Sep. 15, 1998, disclose processes for preparing pellets by mixing of calcium sulfate, water and other medicaments to provide controlled release of calcium sulfate and medicaments.

Snyder, U.S. Pat. No. 5,425,769, issued Jun. 20, 1995, discloses a composition for an artificial bone substitute material consisting of collagen in a calcium sulfate matrix which can be rendered porous by a foaming agent. The composition is adaptable for osseous repair by adjusting the collagen and calcium sulfate in varying ratios to suit particular applications and including admixtures of growth factors.

Sottosanti, U.S. Pat. No. 5,366,507, discloses a composition for use in bone tissue regeneration, the composition containing a barrier material and a graft material. The barrier material can be calcium sulfate, while the graft material may consist of a composite graft material containing demineralized, freeze-dried, allogeneic bone and calcium sulfate.

Sottosanti, U.S. Pat. No. 5,569,308, discloses a method for use in bone tissue regeneration including first filling a graft site with graft material, and then placing a layer of barrier material over at least a portion of the graft material. The barrier material can be calcium sulfate, while the graft material may consist a composite graft material containing demineralized, freeze-dried, allogeneic bone and calcium sulfate.

Hanker et al, "Setting of Composite Hydroxylapatite/Plaster Implants with Blood 5 for Bone Reconstruction," *Proceedings of the 44th Annual Meeting of the Electron Microscopy Society of America*, Copyright 1986, discloses using blood as the only moistening agent in a plaster or plaster/HA mixture as long as accelerator salts are utilized, and suggests that the putty-like consistency of such compositions offers distinct advantages in moldability and workability.

Osteotech, Inc., of Shrewsbury, N.J., markets a bone graft substitute under the mark Grafton®. It is comprised of demineralized bone matrix and glycerol as a carrier material. The carrier material, glycerol, is a viscous, gel-like, weak alcohol that is hydrophilic and water-soluble. It is recognized by the Food and Drug Administration as a "Generally Regarded As Safe" substance.

DePuy, Inc., of Warsaw, Ind., markets a bone graft substitute under the mark DynaGraft®. It is comprised of demineralized bone matrix and poloxamer as a carrier material. Poloxamer is a reverse phase polymer which becomes more viscous with increasing temperature.

Nothing in the known prior art discloses or suggests a bone graft substitute composition including calcium sulfate, a mixing solution such as sterile water, and a plasticizing substance such as carboxymethylcellulose, and having an extended set time and sufficient robustness to withstand fluid impact with minimal erosion.

SUMMARY OF THE INVENTION

A basic concept of the present invention is to provide bone graft substitute composition having an extended set time and sufficient robustness to withstand fluid impact with minimal erosion for expanded clinical applications.

The bone graft substitute composition of the present invention comprises, in general, calcium sulfate; a mixing solution such as sterile water; and a plasticizing substance such as carboxymethylcellulose.

One object of the present invention is to provide a bone graft substitute composition that can be mixed into a paste and then loaded into a syringe and ejected for an extended period of time (e.g., more than ten minutes).

Another object of the present invention is to provide a bone graft substitute composition that can be mixed into a putty and then handled and formed into desired shapes for an extended period of time (e.g., more than ten minutes).

BRIEF DESCRIPTION OF THE DRAWING

The FIGURE is a plot of displacement (mm) vs. time (sec) for certain embodiments of bone graft substitute compositions.

DETAILED DESCRIPTION

The bone graft substitute composition of the present invention comprises, in general, a quantity of calcium sulfate, a quantity of fluid (e.g., sterile water), and a quantity of a plasticizing substance (e.g., methylcellulose) which provides a resultant composition that is robust and has an extended set time. The extended set time of the resultant composition provides a useful working time of at least 5 minutes to allow sufficient time for a surgeon to properly apply the bone graft substitute composition, while the robustness of the resultant composition allows the implanted composition to withstand the typical pressure of body fluids, irrigation fluids and/or suctioning with minimal material erosion, disintegration or dissolution.

The bone graft substitute composition of the present invention may comprise a mixture of calcium sulfate; a mixing solution selected from the group consisting of sterile water, inorganic salts, and cationic surface active agents including sodium chloride, phosphate buffered saline, potassium chloride, sodium sulfate, potassium sulfate, EDTA, ammonium sulfate, ammonium acetate, and sodium acetate, etc.; and a plasticizing substance selected from the group consisting of cellulose derivatives including sodium carboxymethylcellulose, methylcellulose, hydroxypropyl methylcellulose, hydroxypropylcellulose, ethylcellulose, hydroxethylcellulose and cellulose acetate butyrate, and higher molecular weight alcohols including glycerol and vinyl alcohols, etc. The bone graft substitute composition may include demineralized bone matrix. One formulation of the composition may be approximately 100 parts calcium sulfate by weight, 11.1 parts carboxymethylcellulose by weight, 185.2 parts water by weight, and 69.4 parts demineralized bone matrix by weight. Another formulation of the composition may be approximately 100 parts calcium sulfate by weight, 6.3 parts carboxymethylcellulose by weight, and 31 parts water by weight. Another formulation of the composition may be approximately 100 parts calcium sulfate by weight, 1.2 parts carboxymethylcellulose by weight, and 31 parts water by weight. Another formulation of the composition maybe approximately 80-120 parts calcium sulfate by weight, 1-40 parts carboxymethylcellulose by weight, and 21-250 parts water by weight. The composition may include a bioactive agent selected from the group consisting of demineralized bone matrix, growth factors, hyaluronic acid, bone morphogenic proteins, bone autograft, and bone marrow, etc. The composition may include sodium bicarbonate. For example, the composition may include 0.1-2% sodium bicarbonate by weight for creating a porous structure in the resultant composition. Possible embodiments of the bone graft substitute composition of the present invention may include at least one additive selected from the group consisting of antiviral agent, antimicrobial agent, antibiotic agent, amino acid, peptide, vitamin, inorganic element, protein synthesis co-factor, hormone, endocrine tissue, synthesizer, enzyme, polymer cell scaffolding agent with parenchymal cells, angiogenic drug, demineralized bone powder, collagen lattice, antigenic agent, cytoskeletal agent, mesenchymal stem cells, bone digester, antitumor agent, cellular attractant, fibronectin, growth hormone, cellular attachment agent, immunosuppressant, nucleic acid, surface active agent, calcium phosphate materials, such as hydroxyapatite or tricalcium phosphate, penetration enhancer, bone allograft, and chunks, shards, and/or pellets of calcium sulfate.

Preferred Embodiment 1

An injectable bone graft substitute composition having the following preferred formulation: 100 parts by weight of medical grade calcium sulfate hemihydrate (MGCSH), 11.1 parts by weight of carboxymethylcellulose (CMC), 69.4 parts by weight of demineralized bone matrix (DBM), and 162 parts by weight of sterile water.

The preferred method for mixing this putty bone graft substitute composition comprises the following steps: (1) dry blend the powder components (i.e., the calcium sulfate hemihydrate, carboxymethylcellulose, and demineralized bone matrix); (2) add the sterile water; and (3) mix or stir all components for approximately 30 seconds to one minute or until the desired putty-like consistency is achieved.

The resultant injectable bone graft substitute composition has the following characteristic/criteria:

Handability—the resultant composition should: (a) be a single cohesive bolus; (b) be able to be handled and manipulated with minimal to no material transfer (sticking) to latex gloved hand; (c) be able to be handled without material crumbling or falling apart; and (d) exhibit minimal cracking or "tearing" with extreme manipulation, e.g., hard squeezing;

Ejectability—the resultant composition should: (a) be able to be easily manipulated, e.g., rolled into a long cylinder or other suitable shape, so as to be manually placed into an appropriate injection apparatus, e.g., a syringe; and (b) be able to be ejected through a ⅛ inch (0.3175 centimeter) diameter orifice with relatively little pressure required; and Robustness—the resultant composition, after being placed or injected into or onto the desired location, should be able to withstand body fluids, reasonable irrigation fluids and/or suctioning with minimal material erosion, disintegration or dissolution.

Preferred Embodiment 2

A putty bone graft substitute composition having the following preferred formulation: 100 parts by weight of medical grade calcium sulfate hemihydrate (MGCSH), 11.1 parts by weight of carboxymethylcellulose (CMC), and 47 parts by weight of sterile water.

The preferred method for mixing this putty bone graft substitute composition comprises the following steps: (1) dry blend the powder components (i.e., the calcium sulfate hemihydrate, and carboxymethylcellulose); (2) add the sterile water; and (3) mix or stir all components for approximately 30 seconds to one minute or until the desired putty-like consistency is achieved.

The resultant putty bone graft substitute composition has the following characteristic/criteria:

Handability—the resultant composition should: (a) be a single cohesive bolus; (b) be able to be handled and manipulated with minimal to no material transfer (sticking) to latex gloved hand; (c) be able to be handled without material crumbling or falling apart; and (d) exhibit minimal cracking or "tearing" with extreme manipulation, e.g., hard squeezing; and Robustness—the resultant composition, after being placed or injected into or onto the desired location, should be able to withstand body fluids, reasonable irrigation fluids and/or suctioning with minimal material erosion, disintegration or dissolution.

Preferred Embodiment 3

A paste bone graft substitute composition having the following preferred formulation: 100 parts by weight of medical grade calcium sulfate hemihydrate (MGCSH), 1.2 parts by weight of carboxymethylcellulose (CMC), and 31 parts by weight of sterile water.

The preferred method for mixing this putty bone graft substitute composition comprises the following steps: (1) dry blend the powder components (i.e., the calcium sulfate hemihydrate, and carboxymethylcellulose); (2) add the sterile water; and (3) mix or stir all components for approximately 30 seconds to one minute or until the desired putty-like consistency is achieved.

The resultant paste bone graft substitute composition has the following characteristic/criteria:

Ejectability—the resultant composition should be able to be ejected through a ⅛ inch (0.3175 centimeter)diameter orifice with relatively little pressure required.

Preferred Embodiment 4

A bone graft substitute composition having the following preferred formulation: approximately 80-120 parts medical grade calcium sulfate hemihydrate by weight; approximately 21-250 parts sterile water by weight; and approximately 1-40 parts sodium carboxymethylcellulose by weight. This preferred formulation may include approximately 10-100 parts demineralized bone matrix by weight.

The preferred method for mixing this bone graft substitute composition comprises the following steps: (1) dry blend the powder components (i.e., the calcium sulfate hemihydrate, and sodium carboxymethylcellulose, and, if included, the demineralized bone matrix); (2) add the sterile water; and (3) mix or stir all components for approximately 30 seconds to one minute or until the desired consistency is achieved.

The resultant bone graft substitute composition has the following characteristic/criteria:

Handability—the resultant composition should: (a) be a single cohesive bolus; (b) be able to be handled and manipulated with minimal to no material transfer (sticking) to latex gloved hand; (c) be able to be handled without material crumbling or falling apart; and (d) exhibit minimal cracking or "tearing" with extreme manipulation, e.g., hard squeezing;

Ejectability—the resultant composition should: (a) be able to be easily manipulated, e.g., rolled into a long cylinder or other suitable shape, so as to be manually placed into an appropriate injection apparatus, e.g., a syringe; and (b) be able to be ejected through a ⅛ inch (0.3175 centimeter) diameter orifice with relatively little pressure required; and Robustness—the resultant composition, after being placed or injected into or onto the desired location, should be able to withstand body fluids, reasonable irrigation fluids and/or suctioning with minimal material erosion, disintegration or dissolution.

Preferred Embodiment 5

In some preferred embodiments, the bone graft substitute composition includes calcium sulfate, e.g., calcium sulfate hemihydrate; a mixing solution, e.g., sterile water; and a plasticizing substance, e.g., hyaluronic acid or a cellulose derivative such as methylcellulose. The plasticizing substance can include, for example, sodium carboxymethylcellulose, methylcellulose, hydroxypropyl cellulose, hydroxypropyl methyl cellulose, ethylcellulose, hydroxyethylcellulose, and/or cellulose acetate butyrate. The mixing solution can include, for example, sterile water, inorganic salt, cationic surface active agent, bone marrow aspirate, platelet concentrate, blood, pharmaceutical additives in solution, or combinations of these materials. Examples of additives are medicaments or pesticides. Examples of medicaments are antibiotics, chemotherapeutic agents, growth factors, and analgesics. Examples of antibiotics are tetracycline hydrochloride, vancomycin, cephalosporins, and aminoglycocides such as tobramycin and gentamicin. Examples of chemotherapeutic agents are cisplatinum, ifosfamide, methotrexate, and doxorubicin hydrochloride (Adriamycin®). Examples of growth factors are transforming growth factor beta (TGF-Beta), bone morphogenic protein (BMP), basic fiberblast growth factor, platelet-derived growth factor, and other polypeptide growth factors. Examples of analgesics are anesthetics such as lidocaine hydrochloride (Xylocaine®), bipivacaine hydrochloride (Marcaine®), and non-steroidal anti-inflammatory drugs such as ketorolac tromethamine (Toradol®). The cationic surface active agent can include sodium chloride, phosphate buffered saline, potassium chloride, sodium sulfate, ammonium sulfate, ammonium acetate, or sodium acetate.

Generally, the bone graft substitute composition includes a given amount of calcium sulfate, e.g., normalized to 100 parts by weight of $CaSO_4 \cdot \frac{1}{2}H_2O$; an amount of the plasticizing substance sufficient to provide a good biological response, e.g., about 1 to about 10 parts, or about 1 to about 7 parts, or about 2 to about 6 parts, by weight; and a sufficient amount of the mixing solution to provide good handability, e.g., about 20 to about 40 parts, or about 20 to about 35 parts, by weight, such that the composition can be conveniently handled and shaped. For a bone graft composition having $CaSO_4 \cdot \frac{1}{2}H_2O$ and sterile water as the mixing solution, specific compositions are a function of the plasticizing substance used in the composition.

In an embodiment having hydroxypropyl cellulose (HPC) as the plasticizing substance, the composition can include 100 parts by weight of calcium sulfate, e.g., $CaSO_4 \cdot \frac{1}{2}H_2O$; about 2 to about 7 parts, e.g., about 3 parts, by weight of HPC; and about 26 to about 32 parts, e.g., about 28 parts, by weight of the mixing solution, e.g., sterile water.

In an embodiment having hydroxypropyl methyl cellulose (HPMC) as the plasticizing substance, the composition can include 100 parts by weight of calcium sulfate, e.g., $CaSO_4 \cdot \frac{1}{2}H_2O$; about 1 to about 6 parts, e.g., about 2 parts, by weight of HPMC; and about 23 to about 32 parts, e.g., about 25 parts, by weight of the mixing solution, e.g., sterile water.

In an embodiment having hyaluronic acid as the plasticizing substance, the composition can include 100 parts by weight of calcium sulfate, e.g., $CaSO_4 \cdot \frac{1}{2}H_2O$; about 4 to about 6 parts, e.g., about 5 parts, by weight of hyaluronic acid; and about 23 to about 40 parts, e.g., about 30 to about 35 parts, by weight of the mixing solution, e.g., sterile water.

In yet another embodiment, the composition can include about 100 parts by weight of the calcium sulfate hemihydrate, about 25 to about 65 parts by weight of the mixing solution, e.g., water, and about 1.5 to about 8 parts by weight of methylcellulose. For example, the composition can include about 100 parts by weight of the calcium sulfate, e.g., calcium sulfate hemihydrate, about 33.6 parts by weight of the mixing solution, e.g., water, and about 5.25 parts by weight of methylcellulose.

The compositions are formed according to the methods described above. Powder components (e.g., calcium sulfate and plasticizing substance) are dry blended. The mixing solution, e.g., water, is added to the powder components, e.g., prior to use in the operating room, and the mixture is mixed or stirred for about 30-60 seconds or until a desired consistency is achieved.

The resulting bone graft substitute composition is a paste or putty having similar handability, ejectability and/or robustness as described above.

The substitute composition can be handled and shaped such that it can be conveniently positioned and secured into a surgical site. The composition can set up relatively hard, e.g., it can be used as an interoperative structural support, it can be resistant to substantial collapse, or it can withstand fluid impact without substantial erosion. The substitute composition has relatively low to no risk of transmitting infectious disease because, for example, it does not include biological materials such as materials from a cadaver. The composition is relatively inexpensive to produce.

The resulting bone graft substitute can also be used as a carrier, for example, by mixing it with other materials, such as, for example, allografts, antibiotics, growth factors, cancellous bone chips, or synthetically derived or naturally derived chips of minerals such as calcium phosphate or calcium carbonate. This can provide the composition with versatility and flexibility by allowing a user to formulate a mixed composition according to a desired application.

Preferred Embodiment 6

Other preferred embodiments of a bone graft substitute composition include calcium sulfate, e.g., calcium sulfate hemihydrate, demineralized bone matrix, allograft materials, preferably, cancellous bone chips (an osteoconductive substrate) from a cadaver sufficient to provide a desired texture, a plasticizing substance sufficient to provide a good biological response, and a mixing solution sufficient to provide a good handability. The plasticizing substance can include carboxymethylcellulose, e.g., sodium carboxymethylcellulose, methylcellulose, hydroxypropyl methyl cellulose, ethylcellulose, hydroxyethylcellulose, and/or cellulose acetate butyrate. The mixing solution can include, for example, sterile water, inorganic salt, cationic surface active agent, bone marrow aspirates, platelet concentrates, blood, pharmaceutical additives, or combinations of these materials. Examples of additives are listed in Preferred Embodiment 5. The cationic surface active agent can include sodium chloride, phosphate buffered saline, potassium chloride, sodium sulfate, ammonium sulfate, ammonium acetate, or sodium acetate. The cancellous bone can have a particle size of about 1-10 mm, e.g., about 1-6.7 mm, about 1-5.6 mm, about 1-4 mm, or about 4-10 mm.

Generally, the composition can include about 80 to about 120 parts by weight of calcium sulfate, about 10 to about 100 parts by weight of demineralized bone matrix, about 10 to about 100 parts by weight of allograft materials, about 1 to about 40 parts by weight of a plasticizing substance, and about 21 to about 250 parts by weight of a mixing solution. Preferably, the composition includes about 90 to about 110 parts by weight of calcium sulfate, about 10 to about 50 parts by weight of demineralized bone matrix, about 15 to about 50 parts by weight of cancellous bone, about 5 to about 20 parts by weight of a plasticizing substance, and about 80 to about 120 parts by weight of a mixing solution. More preferably, the composition includes about 98 to about 102 parts by weight of calcium sulfate, about 13 to about 23 parts by weight of demineralized bone matrix, about 24 to about 33 parts by weight of cancellous bone, about 15 to about 20 parts by weight of a plasticizing substance, and about 95 to about 105 parts by weight of a mixing solution. Most preferably, the composition includes about 100 parts by weight of calcium sulfate, about 18 to about 19 parts, e.g., about 18 parts, by weight of demineralized bone matrix, about 27 to about 28 parts, e.g., about 27.6 parts, by weight of cancellous bone, about 17 to about 18 parts, e.g., about 17.6 parts, by weight of a plasticizing substance, and about 101 to about 102 parts, e.g., about 101 parts, by weight of a mixing solution.

The compositions are formed according to the methods described above. Powder components (e.g., calcium sulfate hemihydrate, demineralized bone matrix, cancellous bone chips, and carboxymethylcellulose) are dry blended. The mixing solution, e.g., water, is added to the powder components, and the mixture is mixed or stirred for about 30-60 seconds or until a desired consistency is achieved.

In some embodiments, the calcium sulfate, demineralized bone matrix, and the plasticizing substance can be packaged together in a first container, e.g., a vial; and the allograft material, e.g., cancellous bone chip, can be packaged in a second container. A user, e.g., a surgeon, can customize a composition by blending the allograft material with the contents of the first vial and the mixing solution to form a composition with the desired texture.

In some circumstances, the first container can contain a predetermined amount of allograft material, e.g., about 10 parts of cancellous bone chips; and the second container can contain a predetermined amount of allograft material, e.g., up to about 90 parts of cancellous bone chips. In addition to allowing the user to form a composition by blending the mixing solution with only the contents of first container, this allows the user to blend additional allograft material into the composition to a desired texture.

The resulting bone graft substitute composition is a paste or putty having similar handability, ejectability and/or robustness as described above. The cancellous bone chips can provide the composition with good structural support, and the relatively large surface area of the cancellous bone chips can provide the composition with good osteoconduction.

Preferred Embodiment 7

Other preferred embodiments of a bone graft substitute composition include calcium sulfate, e.g., calcium sulfate hemihydrate, demineralized bone matrix, allograft materials, preferably, cancellous bone chips (an osteoconductive substrate) from a cadaver sufficient to provide a desired texture, a plasticizing substance sufficient to provide a good biological response, and a mixing solution sufficient to provide a good handability. The plasticizing substance can include carboxymethylcellulose, e.g., sodium carboxymethylcellulose, methylcellulose, hydroxypropyl methyl cellulose, ethylcellulose, hydroxyethylcellulose, and/or cellulose acetate butyrate. The mixing solution can include, for example, sterile water, inorganic salt, cationic surface active agent, bone marrow aspirates, platelet concentrates, blood, pharmaceutical additives, or combinations of these materials. Examples of additives are listed in Preferred Embodiment 5. The cationic surface active agent can include sodium chloride, phosphate buffered saline, potassium chloride, sodium sulfate, ammonium sulfate, ammonium acetate, or sodium acetate. The cancellous bone can have a particle size of about 1-10 mm, e.g., about 1-4 mm.

Generally, the composition can include about 80 to about 120 parts by weight of calcium sulfate, about 10 to about 100 parts by weight of demineralized bone matrix, about 20 to about 130 parts by weight of allograft materials, e.g., cancellous bone, about 1 to about 40 parts by weight of a plasticizing substance, and about 21 to about 250 parts by weight of a mixing solution. Preferably, the composition includes about 90 to about 110 parts by weight of calcium sulfate, about 10 to about 50 parts by weight of demineralized bone matrix, about 15 to about 50 parts by weight of allograft materials, about 5 to about 20 parts by weight of a plasticizing substance, and about 80 to about 120 parts by weight of a mixing solution. More preferably, the composition includes about 98 to about 102 parts by weight of calcium sulfate, about 13 to about 23 parts by weight of demineralized bone matrix, about 37 to about 46 parts by weight of allograft materials, about 15 to about 20 parts by weight of a plasticizing substance, and about 95 to about 105 parts by weight of a mixing solution. Most preferably, the composition includes about 100 parts by weight of calcium sulfate, about 18 to about 19 parts, e.g., about 18 parts, by weight of demineralized bone matrix, about 40 to about 42 parts, e.g., about 41 parts, by weight of allograft materials, about 17 to about 18 parts, e.g., about 17.6 parts, by weight of a plasticizing substance, and about 101 to about 102 parts, e.g., about 101 parts, by weight of a mixing solution.

The compositions are formed according to the methods described above. Powder components (e.g., calcium sulfate hemihydrate, demineralized bone matrix, cancellous bone chips, and carboxymethylcellulose) are dry blended. The mixing solution, e.g., water, is added to the powder components, and the mixture is mixed or stirred for about 30-60 seconds or until a desired consistency is achieved.

In some embodiments, the calcium sulfate, demineralized bone matrix, and the plasticizing substance can be packaged together in a first container, e.g., a vial; and the allograft material, e.g., cancellous bone chip, can be packaged in a second container. A user, e.g., a surgeon, can customize a composition by blending the allograft material with the contents of the first vial and the mixing solution to form a composition with the desired texture.

In some circumstances, the first container can contain a predetermined amount of allograft material, e.g., about 10 parts of cancellous bone chips; and the second container can contain a predetermined amount of allograft material, e.g., up to about 90 parts of cancellous bone chips. In addition to allowing the user to form a composition by blending the mixing solution with only the contents of first container, this allows the user to blend additional allograft material into the composition to a desired texture.

The resulting bone graft substitute composition is a paste or putty having similar handability, ejectability and/or robustness as described above. The cancellous bone chips can provide the composition with good structural support, and the relatively large surface area of the cancellous bone chips can provide the composition with good osteoconduction.

Preferred Embodiment 8

Still other preferred embodiments of a bone graft substitute composition include calcium sulfate, e.g., calcium sulfate hemihydrate, demineralized bone matrix, allograft materials, preferably, cancellous bone chips (an osteoconductive substrate) from a cadaver sufficient to provide a desired texture, a plasticizing substance sufficient to provide a good biological response, and a mixing solution sufficient to provide a good handability. The plasticizing substance can include carboxymethylcellulose, e.g., sodium carboxymethylcellulose, methylcellulose, hydroxypropyl methyl cellulose, ethylcellulose, hydroxyethylcellulose, and/or cellulose acetate butyrate. The mixing solution can include, for example, sterile water, inorganic salt, cationic surface active agent, bone marrow aspirates, platelet concentrates, blood, pharmaceutical additives, or combinations of these materials. Examples of additives are listed in Preferred Embodiment 5. The cationic surface active agent can include sodium chloride, phosphate buffered saline, potassium chloride, sodium sulfate, ammonium sulfate, ammonium acetate, or sodium acetate. The cancellous bone can have a particle size of about 1-10 mm, e.g., about 4-10 mm, or about 4-9.5 mm. Without wishing to be bound to theory, it is believed that using cancellous bone of increased particle size provides the composition with enhanced capacity for fluid absorption. As a result, the composition can be loaded with a relatively large amount of the mixing solution, such as platelet concentrates or bone marrow aspirates, that can be delivered to a surgical site. In some embodiments, the powder components of the composition can absorb up to a 1:1 ratio of mixing solution by volume.

Generally, the composition can include about 80 to about 120 parts by weight of calcium sulfate, about 10 to about 120 parts by weight of demineralized bone matrix, about 20 to about 150 parts by weight of allograft materials, e.g., cancellous bone, about 1 to about 40 parts by weight of a plasticizing substance, and about 50 to about 300 parts by weight of a mixing solution. Preferably, the composition includes about 90 to about 110 parts by weight of calcium sulfate, 10 to about 60 parts by weight of demineralized bone matrix, about 40 to about 120 parts by weight of allograft materials, about 5 to about 20 parts by weight of a plasticizing substance, and about 140 to about 180 parts by weight of a mixing solution. More preferably, the composition includes about 98 to about 102 parts by weight of calcium sulfate, about 25 to about 35 parts by weight of demineralized bone matrix, about 44 to about 110 parts by weight of allograft materials, about 15 to about 20 parts by weight of a plasticizing substance, and about 160 to about 170 parts by weight of a mixing solution. Most preferably, the composition includes about 100 parts by weight of calcium sulfate, about 30 to about 32 parts, e.g., about 31 parts, by weight of demineralized bone matrix, about 99 to about 105 parts, e.g., about 102 parts, by weight of allograft materials, about 17 to about 18 parts, e.g., about 17.6 parts, by weight of a plasticizing substance, and about 162 to about 168 parts, e.g., about 164 parts, by weight of a mixing solution.

The compositions are formed according to the methods described above. Powder components (e.g., calcium sulfate hemihydrate, demineralized bone matrix, cancellous bone chips, and carboxymethylcellulose) are dry blended. The mixing solution, e.g., water, is added to the powder components, and the mixture is mixed or stirred for about 130-60 seconds or until a desired consistency is achieved.

In some embodiments, the calcium sulfate, demineralized bone matrix, and the plasticizing substance can be packaged together in a first container, e.g., a vial; and the allograft material, e.g., cancellous bone chip, can be packaged in a second container. A user, e.g., a surgeon, can customize a composition by blending the allograft material with the contents of the first vial and the mixing solution to form a composition with the desired texture.

In some circumstances, the first container can contain a predetermined amount of allograft material, e.g., about 45 parts of cancellous bone chips; and the second container can contain a predetermined amount of allograft material, e.g., up to about 150 parts of cancellous bone chips. In addition to allowing the user to form a composition by blending the mixing solution with only the contents of first container, this allows the user to blend additional allograft material into the composition to a desired texture. The amount of allograft material in the first and second containers can vary within the ranges provided above.

The resulting bone graft substitute composition is a paste or putty having similar handability, ejectability and/or robustness as described above. The cancellous bone chips can provide the composition with good structural support, and the relatively large surface area of the cancellous bone chips can provide the composition with good osteoconduction.

Preferred embodiments 5-8 can be packaged as kits that allow the user to customize a desired composition by combining the mixing solution with the desired powder components according to a desired use, texture, consistency, and/or concentration of a particular component, such as cancellous bone.

Tests

The majority of tests done to date on the bone graft substitute composition of the present invention basically consist of mixing a specific formulation and then assessing and recording the mixing, handling, consistency, and injectability properties of the resultant material.

Formulation Tests

Injectable Bone Graft Substitute Composition: Formulations with various types and amounts of carboxymethylcellulose and demineralized bone matrix have been tested. Specific examples include: (1) carboxymethylcellulose percentages of 1-10% by weight; (2) types of carboxymethylcellulose have included high viscosity, medium viscosity, and low viscosity from 3 vendors (e.g., Aqualon® 7HF PH sodium carboxymethylcellulose from Hercules Incorporated, Hercules Plaza, 1313 North Market Street, Wilmington, Del. 19894-0001); (3) carboxymethylcellulose sterilized by gamma or electronic beam sterilization (medium and low doses); (4) demineralized bone matrix percentages up to 65% by volume; (5) differently processed demineralized bone matrix, air dried and freeze dried; (6) demineralized bone matrix from two vendors (e.g., human freeze dried demineralized bone matrix from AlloSource, 8085 E. Harvard Ave., Denver, Colo. 80231); and (7) animal demineralized bone matrix, including bovine and canine.

For all these formulations, varying amounts of water, between 31-200 parts by weight, have been tested. The mixing, handling, consistency, and injectability properties were assessed and formulas chosen such that they met the mixing, handability, ejectability, and robustness characteristics/criteria stated hereinabove.

Paste And Putty Bone Graft Substitute Composition: These were the first tests done and included formulations with compositions having 100 parts by weight medical grade calcium sulfate hemihydrate, and between 1-10% by weight carboxymethylcellulose, and between 31-200 parts by weight water. As was the case with the injectable bone graft substitute composition, mixing, handability, consistency, injectability, and robustness properties were assessed for the different formulations. Specific tests have included: (1) varying the carboxymethylcellulose percentages from 0.25% up to 10% by weight, (2) using inorganic salt solutions including 2% sodium chloride (NaCl) by weight, 2-4% sodium sulfate ($Na_2SO_4$) by weight, and 2% potassium chloride (KCl) by weight.

As with the injectable bone graft substitute composition, varying amounts of water, 31-200 parts by weight, were used.

EXAMPLE 1

The osteoinductive properties of the injectable bone graft substitute composition have been studied using an athymic mouse-intramuscular implantation model. This animal model is widely accepted as the "gold standard" for assessing osteoinductive characteristics of bone graft materials. In this model, a given amount of material is surgically placed into a muscular site. After an implantation period of four weeks, the osteoinductive response is assessed using various analytical methods, including radiography, biochemical analysis (alkaline phosphatase levels and calcium content), and histomorphometry.

In this study, four athymic (nude) male mice (Harlan Sprague Dawley, Inc.) were used for each material group. Two muscle pouches were formed in the right and left gluteal muscles of each mouse and implanted with either: (1) pellets which were manufactured using the composition given in Preferred Embodiment 1, or (2) twenty (20) 5 mg of demineralized bone matrix which had been rehydrated with isotonic saline (0.9% NaCl). The pellets made from Preferred Embodiment 1 were 3.0 mm in diameter, 2.5 mm in height and 25 mg in weight.

After twenty-eight (28) days the animals were sacrificed and the materials explanted. The explants were analyzed for osteoinductive potential by assessing the alkaline phosphatase activity and for new bone growth by histomorphometric analysis of histologic sections.

Samples to be analyzed for alkaline phosphatase activity were minced, sonicated, and extracted with water saturated butanol. The extracts were assayed for protein content using a Pierce BCA Protein Assay Kit (Pierce Chemical Co.) and measuring the conversion of para-nitrophenylphosphate (PNPP) to para-nitrophenol (pNP) with time. The results were expressed as $\mu$mole pNP formed/min/$\mu$g tissue protein.

Samples intended for histomorphometric analyses were prepared using standard histological procedures. The percent viable bone (new bone formation) was quantitated employing computer software (Adobe Photo Shop 3.0.4 and HNIH 1.61), in conjunction with a microscope equipped with a video camera. Data was reported as percent viable bone relative to the total cross-sectional area analyzed.

The alkaline phosphatase levels ($\mu$mole pNP formed/min/$\mu$g tissue protein) and percent viable bone results for the groups of mice implanted with DBM only and with injectable putty manufactured using the composition given in Preferred Embodiment 1 are shown in Table 1.

TABLE 1

Osteoinductive Results
Alkaline Phosphatase Levels and Percent Viable Bone

| Group | Alkaline Phosphatase Levels ($\mu$mole pNP formed/min/$\mu$g tissue protein) | Percent Viable Bone (%) |
|---|---|---|
| DMB only | $2.1 \times 10^{-5} \pm 0.3 \times 10^{-5}$ | 6.5% ± 1.0% |
| Injectable Putty (Preferred Embodiment 1) | $3.0 \times 10^{-5} \pm 0.2 \times 10^{-5}$ | 4.7% ± 0.9% |

EXAMPLE 2

A study was performed on canines to evaluate healing of bone defects using materials with the composition given in Preferred Embodiment 1. The DBM used in these compositions was fresh frozen canine DBM (Veterinarian Transplant Services, Seattle, Wash.). Two methods were used to produce the test materials. The first material group consisted of a blend of DBM, calcium sulfate, and CMC powder that was irradiated sterilized, while the second group mixed canine DBM with the calcium sulfate-CMC blend at the time of surgery.

In this canine animal model, large medullary cylindrical defects (13 mm diameter ×50 mm length)were created bilaterally in the proximal humeri by drilling axially through the greater tubercle. Six to 7 cc of test material were injected into prepared cavities using a large-bore catheter-tip syringe. Left humeri received the premixed material that hand been sterilized and the right humeri received the material mixed intraoperatively which utilized non-irradiated canine DBM. Radiographs of the humeri were obtained preoperative, immediately postoperative, and at 2, 3, and 6 weeks. Following euthanasia after 6 weeks, the explanted humeri were sectioned transversely, radiographed, and processed for plastic imbedded undecalcified histology. The histologic sections were stained with basic fuchsin and toluidine blue and examined by light microscopy.

Post-operative radiographs revealed all test materials to be well contained in the prepared cavities. Normal would healing occurred and there were no postoperative infections. Serial clinical radiographs showed a progressive decrease in materials density with time. No difference was evident between the right and left sides.

Contact radiographs of the cut sections demonstrated no difference in pattern or density of bone filling the right and left defects, non-irradiated and irradiated canine DBM materials groups, respectively. Serial sections for all the dogs showed between 30-100% filling of the defect, with one dog showing almost complete filling for all sections.

Histologically, the nature of new bone formation and the amount of residual material were similar in the right and left defects. In the peripheral one-third of the defects, new bone was present at the margins and haversian surfaces of abundant DBM particles. Residual calcium sulfate was evident, incorporated within slender bone trabeculae, independent of DBM particles. New bone formation in the central aspect of the defects was more variable, with some vascular fibrosus tissue shown. No foreign body or inflammatory response was seen in any of the slides, indicating that the materials had extremely good biocompatibilty.

Thus, materials with compositions given in Preferred Embodiment 1 were shown to be well tolerated by the bone and to heal a large medullary defect 30-100% at six weeks with viable new bone in a canine bone defect model.

EXAMPLE A

The following samples were prepared as described above to determine their ability to resist compression through a mesh.

|  | Sample A | Sample B | Sample C |
| --- | --- | --- | --- |
| $CaSO_4 \cdot \frac{1}{2}H_2O$ | 100 | 100 | 100 |
| Demineralized Bone Matrix | 69.4 | 18 | 31 |
| Cancellous Bone Chips | — | 41 (1-4 mm) | 102 (4-10 mm) |
| Carboxymethylcellulose | 11.1 | 17.6 | 17.6 |
| Sterile Water | 162 | 101 | 164 |

Approximately 10 cc of each sample was placed into a cylinder (about 22 mm in diameter) formed of a mesh (about 2.7 mm grid). The sample was packed in the cylinder to a height of about 29.5-34 mm.

The sample was loaded into a mechanical testing system (Model 1331 Testing System, available from Instron (Canton, Mass.)) with the cylinder oriented vertically. A ram (a 20 mm diameter flat end rod) was placed in the cylinder on top of the sample. A 100 N load was applied in one second. Displacement data were recorded every 0.1 sec (using NotebookPro software, available from Labtech (Andover, Mass.)). FIG. 1 shows the displacement (mm) of Samples A, B, and C (n=1) as a function of time (sec). The samples displayed good resistance to compression. As a result, in some circumstances, the samples may be more likely to be retained in a surgical site, e.g., a cavity, after they are positioned in place.

Although the present invention has been described and illustrated with respect to preferred embodiments and preferred uses therefor, it is not to be so limited since modifications and changes can be made therein which are within the full intended scope of the invention. For example, in embodiments that include cancellous bone, calcium phosphate materials, such as hydroxyapatite or tricalcium phosphate, can be substituted for all or a portion of the cancellous bone.

Other embodiments are within the claims.

What is claimed is:

1. A bone graft substitute composition, comprising:
   about 80 to about 120 parts by weight of calcium sulfate;
   about 10 to about 100 parts by weight of demineralized bone matrix;
   about 20 to about 130 parts by weight of cancellous bone;
   about 1 to about 40 parts by weight of a plasticizing substance; and
   about 21 to about 250 parts by weight of a mixing solution, wherein the cancellous bone has a particle size between about 1 and about 4 mm.

2. The composition of claim 1, wherein the calcium sulfate comprises calcium sulfate hemihydrate.

3. The composition of claim 1, wherein the plasticizing substance comprises a cellulose derivative.

4. The composition of claim 1, wherein the plasticizing substance is selected from a group consisting of sodium carboxymethylcellulose, methylcellulose, hydroxypropyl methyl cellulose, hydroxypropyl cellulose, ethylcellulose, hydroxyethylcellulose, and cellulose acetate butyrate.

5. The composition of claim 1, wherein the mixing solution is selected from a group consisting of sterile water, inorganic salt, and cationic surface active agent.

6. The composition of claim 5, wherein the cationic surface active agent is selected from a group consisting of sodium chloride, phosphate buffered saline, potassium chloride, sodium sulfate, ammonium sulfate, ammonium acetate, and sodium acetate.

7. The composition of claim 1, wherein the mixing solution comprises sterile water.

8. The composition of claim 1, wherein the mixing solution comprises a material selected from a group consisting of bone marrow aspirate, platelet concentrate, blood, an antibiotic, a chemotherapeutic agent, a growth factor, and an analgesic.

9. The composition of claim 1, comprising:
   about 90 to about 110 parts by weight of calcium sulfate;
   about 10 to about 50 parts by weight of demineralized bone matrix;
   about 15 to about 50 parts by weight of cancellous bone;
   about 5 to about 20 parts by weight of a plasticizing substance; and
   about 80 to about 120 parts by weight of a mixing solution.

10. The composition of claim 1, comprising:
    about 98 to about 102 parts by weight of calcium sulfate;
    about 13 to about 23 parts by weight of demineralized bone matrix;
    about 37 to about 46 parts by weight of cancellous bone;
    about 15 to about 20 parts by weight of a plasticizing substance; and
    about 95 to about 105 parts by weight of a mixing solution.

11. The composition of claim 1, comprising:
    about 100 parts by weight of calcium sulfate;
    about 18 to about 19 parts by weight of demineralized bone matrix;
    about 40 to about 42 parts by weight of cancellous bone;
    about 17 to about 18 parts by weight of a plasticizing substance; and about 101 to about 102 parts by weight of a mixing solution.

12. A bone graft substitute composition, comprising: about 80 to about 120 parts by weight of calcium sulfate;
about 10 to about 120 parts by weight of demineralized bone matrix;
about 20 to about 150 parts by weight of cancellous bone;
about 1 to about 40 parts by weight of a plasticizing substance; and
about 50 to about 300 parts by weight of a mixing solution, wherein the cancellous bone has a particle size between about 4 and about 10 mm.

13. The composition of claim 12, wherein the calcium sulfate comprises calcium sulfate hemihydrate.

14. The composition of claim 12, wherein the plasticizing substance comprises a cellulose derivative.

15. The composition of claim 12, wherein the plasticizing substance is selected from a group consisting of sodium carboxymethylcellulose, methylcellulose, hydroxypropyl methyl cellulose, hydroxypropyl cellulose, ethylcellulose, hydroxyethylcellulose, and cellulose acetate butyrate.

16. The composition of claim 12, wherein the mixing solution is selected from a group consisting of sterile water, inorganic salt, and cationic surface active agent.

17. The composition of claim 16, wherein the cationic surface active agent is selected from a group consisting of sodium chloride, phosphate buffered saline, potassium chloride, sodium sulfate, ammonium sulfate, ammonium acetate, and sodium acetate.

18. The composition of claim 12, wherein the mixing solution comprises sterile water.

19. The composition of claim 12, wherein the mixing solution comprises a material selected from a group consisting of bone marrow aspirate, platelet concentrate, blood, an antibiotic, a chemotherapeutic agent, a growth factor, and an analgesic.

20. The composition of claim 12, comprising:
about 90 to about 110 parts by weight of calcium sulfate;
about 10 to about 60 parts by weight of demineralized bone matrix;
about 40 to about 120 parts by weight of cancellous bone;
about 5 to about 20 parts by weight of a plasticizing substance; and
about 140 to about 180 parts by weight of a mixing solution.

21. The composition of claim 12, comprising:
about 98 to about 102 parts by weight of calcium sulfate;
about 25 to about 35 parts by weight of demineralized bone matrix;
about 44 to about 110 parts by weight of cancellous bone;
about 15 to about 20 parts by weight of a plasticizing substance; and
about 160 to about 170 parts by weight of a mixing solution.

22. The composition of claim 12, comprising:
about 100 parts by weight of calcium sulfate;
about 30 to about 32 parts by weight of demineralized bone matrix;
about 99 to about 105 parts by weight of cancellous bone;
about 17 to about 18 parts by weight of a plasticizing substance; and
about 162 to about 168 parts by weight of a mixing solution.

23. A kit for making a bone graft substitute composition, the kit comprising:
a first portion comprising:
about 80 to about 120 parts by weight of calcium sulfate;
about 10 to about 120 parts by weight of demineralized bone matrix;
a first portion of cancellous bone having a particle size between about 4 and about 10 mm; and
about 1 to about 40 parts by weight of a plasticizing substance;
a second portion comprising:
a second portion of cancellous bone having a particle size between about 4 and about 10 mm; and
a third portion comprising:
about 50 to about 300 parts by weight of a mixing solution,
wherein the first and second portions of cancellous bone total about 20 to about 150 parts by weight of cancellous bone.

24. The kit of claim 23, wherein the first portion comprises about 40 to about 50 parts by weight of cancellous bone.

25. A method of preparing a bone graft substitute composition, the method comprising:
providing a first portion comprising:
about 80 to about 120 parts by weight of calcium sulfate;
about 10 to about 120 parts by weight of demineralized bone matrix;
a first portion of cancellous bone having a particle size between about 4 and about 10 mm; and
about 1 to about 40 parts by weight of a plasticizing substance;
providing a second portion comprising:
a second portion of cancellous bone having a particle size between about 4 and about 10 mm, wherein the first and second portions of cancellous bone total about 20 to about 150 parts by weight of cancellous bone;
providing a third portion comprising:
about 50 to about 300 parts by weight of a mixing solution; and
mixing the third portion with the first portion to form a bone graft substitute composition.

26. The method of claim 25, further comprising mixing a portion of the second portion with the third and first portions.

* * * * *